(12) United States Patent
Narula et al.

(10) Patent No.: US 6,920,881 B2
(45) Date of Patent: Jul. 26, 2005

(54) WOUND COVERING PRESSURE RELIEF PADS

(76) Inventors: Vinod Narula, 9805 Silky Dogwood Ct., Louisville, KY (US) 40241; Dipak Narula, 910 Cherokee Rd., Louisville, KY (US) 40204

(*) Notice: Subject to any disclaimer, the term of this patent is extended or adjusted under 35 U.S.C. 154(b) by 551 days.

(21) Appl. No.: 09/891,481

(22) Filed: Jun. 26, 2001

(65) Prior Publication Data

US 2002/0007136 A1 Jan. 17, 2002

Related U.S. Application Data

(60) Provisional application No. 60/214,085, filed on Jun. 27, 2000.

(51) Int. Cl.[7] .............................................. A61F 13/00
(52) U.S. Cl. ........................................ 128/889; 128/894
(58) Field of Search .................... 2/16, 22, 24; 128/892, 128/893, 889, 894

(56) References Cited

U.S. PATENT DOCUMENTS

| | | | |
|---|---|---|---|
| 1,736,515 A | * 11/1929 | Anderson | .................. 128/894 |
| 3,937,218 A | 2/1976 | Gaylord, Jr. | |
| 3,972,328 A | 8/1976 | Chen | |
| 4,278,079 A | * 7/1981 | Simhoni et al. | ............ 128/892 |
| 4,390,519 A | 6/1983 | Sawyer | |
| 4,538,603 A | 9/1985 | Pawelchak et al. | |
| 4,655,767 A | 4/1987 | Woodard et al. | |
| 4,723,322 A | 2/1988 | Shelby | |
| 4,738,257 A | 4/1988 | Meyer et al. | |
| 4,759,354 A | 7/1988 | Quarfoot | |
| 4,773,409 A | 9/1988 | Cilento et al. | |
| 4,777,679 A | 10/1988 | DeLooper | |
| 4,801,291 A | * 1/1989 | Loori | ......................... 604/23 |
| 4,825,486 A | 5/1989 | Kimura et al. | |
| 4,843,666 A | 7/1989 | Elesh et al. | |
| 4,909,244 A | 3/1990 | Quarfoot et al. | |
| 5,010,878 A | * 4/1991 | Kline et al. | ................... 601/27 |
| 5,020,808 A | * 6/1991 | Richards | ..................... 473/589 |
| 5,090,055 A | 2/1992 | McElroy | |
| 5,098,421 A | 3/1992 | Zook | |
| 5,133,821 A | 7/1992 | Jensen | |
| 5,240,135 A | 8/1993 | Lepinoy | |
| 5,282,482 A | 2/1994 | Wilk | |
| 5,636,643 A | 6/1997 | Argenta et al. | |
| 5,657,488 A | 8/1997 | Urelli | |
| 5,681,579 A | 10/1997 | Freeman | |
| 5,827,213 A | 10/1998 | Jensen | |
| 5,882,324 A | 3/1999 | Baranowski | |
| 5,891,074 A | 4/1999 | Cesarczyk | |
| 5,914,125 A | 6/1999 | Andrews et al. | |
| 5,947,914 A | 9/1999 | Augustine | |
| 5,951,366 A | 9/1999 | Stevens | |
| 5,961,480 A | 10/1999 | Augustine | |
| 5,964,721 A | 10/1999 | Augustine | |
| 6,000,403 A | 12/1999 | Cantwell | |
| 6,087,549 A | 7/2000 | Flick | |
| 6,095,894 A | 8/2000 | Stevens | |
| 6,149,613 A | * 11/2000 | Klein | ........................... 602/23 |
| 6,201,164 B1 | 3/2001 | Wulff et al. | |
| 6,241,697 B1 | 6/2001 | Augustine | |
| 6,640,810 B1 | * 11/2003 | Callsen et al. | .............. 128/882 |

* cited by examiner

*Primary Examiner*—Henry Bennett
*Assistant Examiner*—Camtu Nguyen
(74) *Attorney, Agent, or Firm*—J. L. Simunic

(57) ABSTRACT

A pressure relief pad for use by persons suffering from or subject to the formation of decubitus ulcers or bedsores is described. The pressure relief pad is made from viscoelastic foam layers which provide for the redistribution of pressure around an affected or wounded area allowing the wound to heal faster. The contoured viscoelastic foam pad can be positioned over a separately applied dressing or an exudate absorbing material can be included in the pad. The contouring for the pad may be achieved by molding the foam as desired or by using a multiplicity of foam layers joined by adhesive to form the pad.

10 Claims, 13 Drawing Sheets

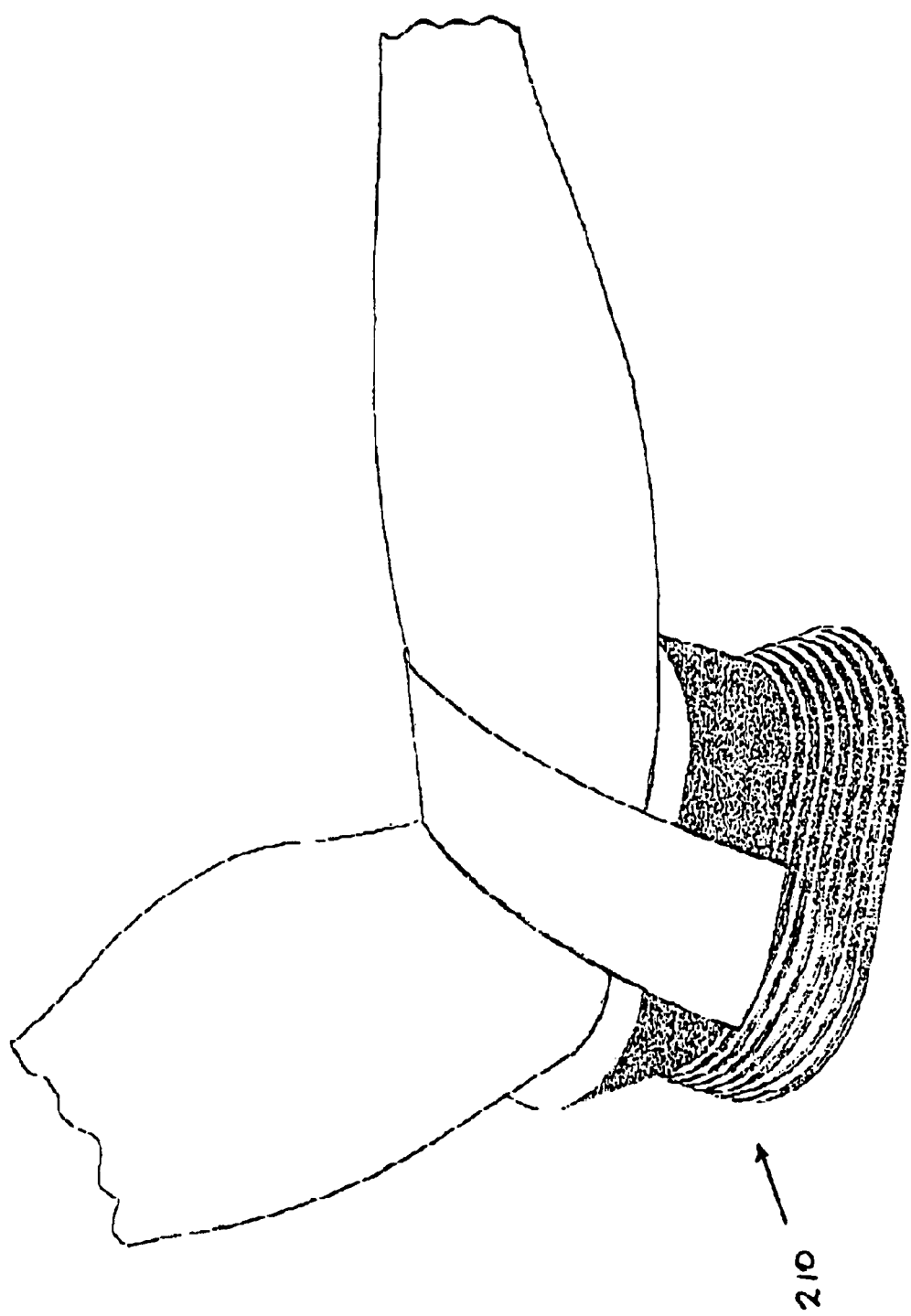

WOUND COVERING PRESSURE RELIEF PADS

This application claims priority to provisional patent application No. 60/214,085, filed on Jun. 27, 2000.

BACKGROUND

The present invention relates to a pressure relief pad for use by persons having limited mobility which may lead to the formation of bedsores, and by persons suffering from bedsores or similar wounds which generate exudates.

When a person has limited mobility or is confined to bed for an extended period of time, poor or compromised circulation can cause blood and other bodily fluids to pool in certain areas of the body—usually at points or regions where a higher degree of pressure is generated between the body and the surface upon which it is resting. If the pressure is not relieved and if the fluids are not forced to move within the body, the area may become devitalized resulting in the breakdown of the integrity of the skin and leading to decubitus ulcers or bedsores, which may become infected.

Some traditional ways for promoting the healing of bedsores include cleansing the wound area, then covering the wound area with a moist dressing; debriding any eschar or surface necrosis, then covering the area with a moist dressing; or removing all devitalized tissue if the wound is extremely deep, covering the area with dry dressings until the bleeding is controlled, then covering the wound area with a moist dressing. As is known in the art, the wound area should be covered with a dressing that will keep the ulcer bed continuously moist but keep the surrounding intact skin dry. For wounds that do not respond to the above treatments, the American Medical Directors Association suggests protecting the wound area from the adverse affects of pressure, friction, and shear. For example, the wound area can be supported on a low-air-loss mattress or on an air-fluidized bed.

SUMMARY

The present invention relates to a pressure relief pad for use by persons suffering from or subject to the formation of decubitus ulcers or bedsores. The pressure relief pad is made from viscoelastic foam layers which provide for the redistribution of pressure around an affected or wounded area allowing the wound to heal faster. The pressure relief pad can be applied, for example, over a bedsore to aid the healing of the bedsore. The pad can also be used over an area that is likely to develop or redevelop a bedsore to redistribute the pressure around the target area, thereby preventing bodily fluids from pooling in that area.

In an embodiment of the pressure relief pad, a pad made from contoured viscoelastic foam is positioned over a separately applied dressing. In an alternative embodiment of the pressure relief pad, a multiplicity of foam layers joined by adhesive layers are used to form the pad. In another alternative embodiment, the pad includes an exudate absorbing material that can be placed directly against a person's open wound. In another alternative embodiment, a cavity within the pad can be filled with a gelled material to aid the wound healing process.

SUMMARY OF THE FIGURES

FIG. 7 is a cross-sectional view of the pad of FIG. 5 taken along line 7—7;

DETAILED DESCRIPTION

The present invention relates to a wound covering pressure relief pad for use by persons suffering from or subject to the formation of decubitus ulcers or bedsores. The pressure relief pad is made from viscoelastic foam layers which provide for the redistribution of pressure around an affected or wounded area allowing the wound to heal faster. The pressure relief pad depicted in the various Figures is selected solely for the purpose of illustrating the invention. Other and different wound covering pressure relief pads may utilize the inventive features described herein as well.

Figure 1:
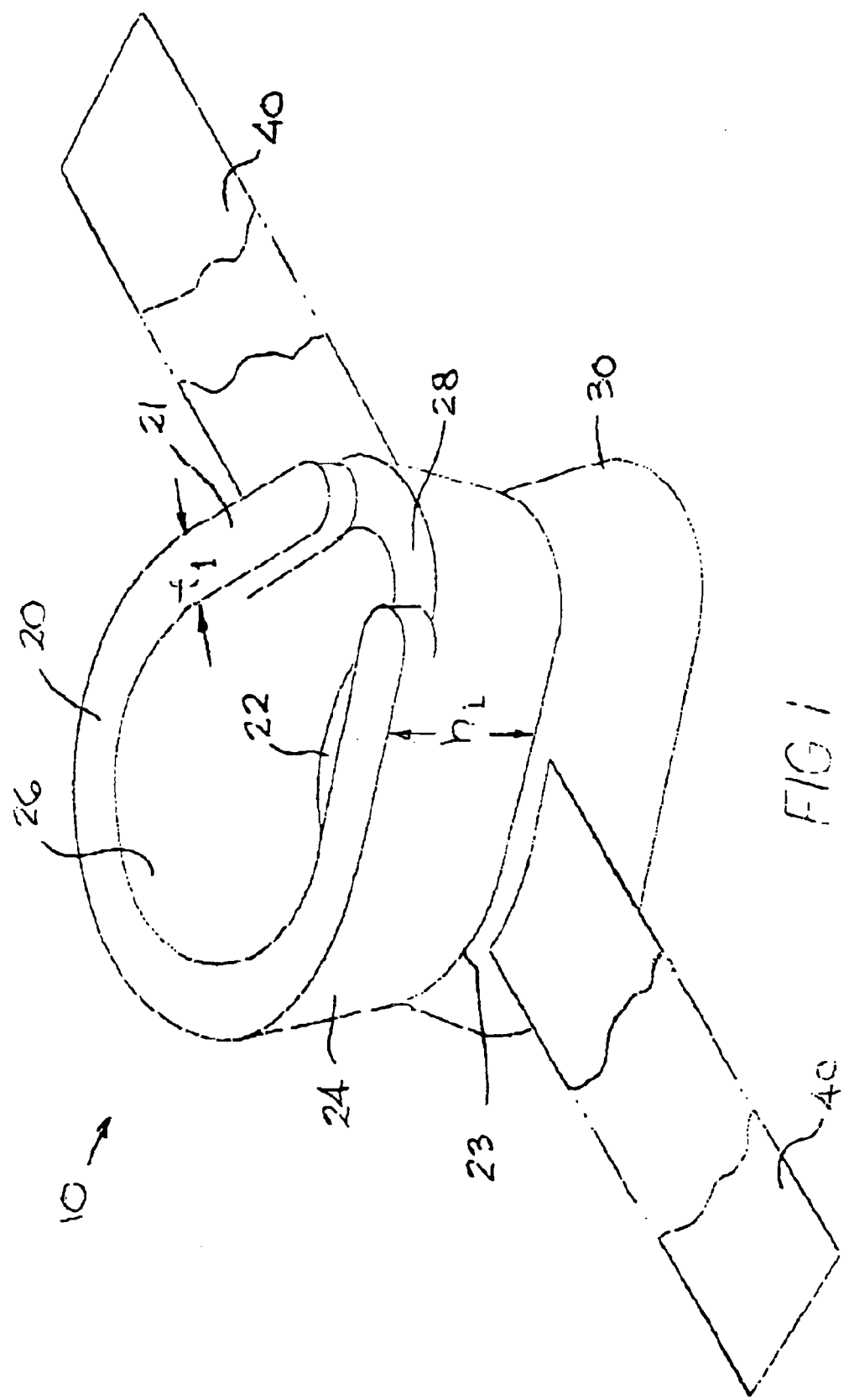
FIG. 1 is a perspective view of a pressure relief pad to fit over the heel made in accordance with the present invention.
Figure 2:
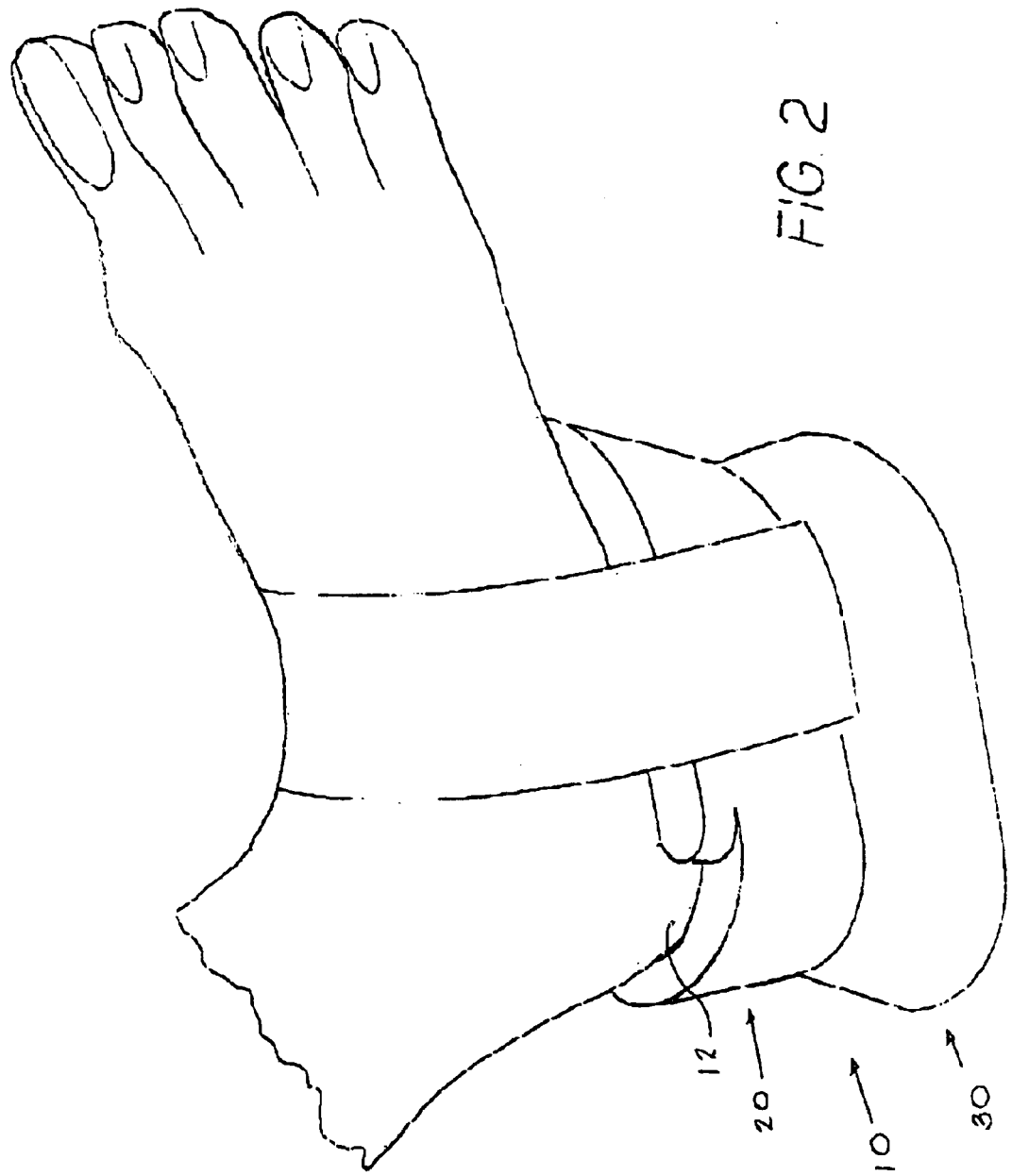
FIG. 2 is a side perspective view of the pad of FIG. 1 positioned over a patient's heel.

Reference is first made to FIGS. 1–4 in which a wound covering pressure relief pad constructed in accordance with the present invention is generally noted by the character numeral 10. The pad 10 has a contoured shell 20, a resting platform 30 and an attachment strap 40. As shown in FIG. 2, the pad of FIG. 1 is contoured to fit over a patient's heel 12. However, the pad 10 may be contoured to fit over or against other body regions, such as the elbow, head, back or hip.

Referring again to FIG. 1, the contoured shell 20 of the wound covering pad 10 has an essentially flat base 22, having a periphery 23. A side 24, which has a predetermined thickness $t_1$, projects upwardly from the base 22 adjacent to the periphery 23 by a predetermined distance $h_1$. For the heel pad 10, the side 24 flares outward slightly to allow the patient's heel 12 and part of the foot to fit within a cavity or cup 26 formed by the base 22 and the wall 24. The cup 26 includes a top edge or rim 21 which may be continuous, or it 21 may include a recessed area 28 to allow for a better fit about the patient's heel and ankle.

Figure 3:
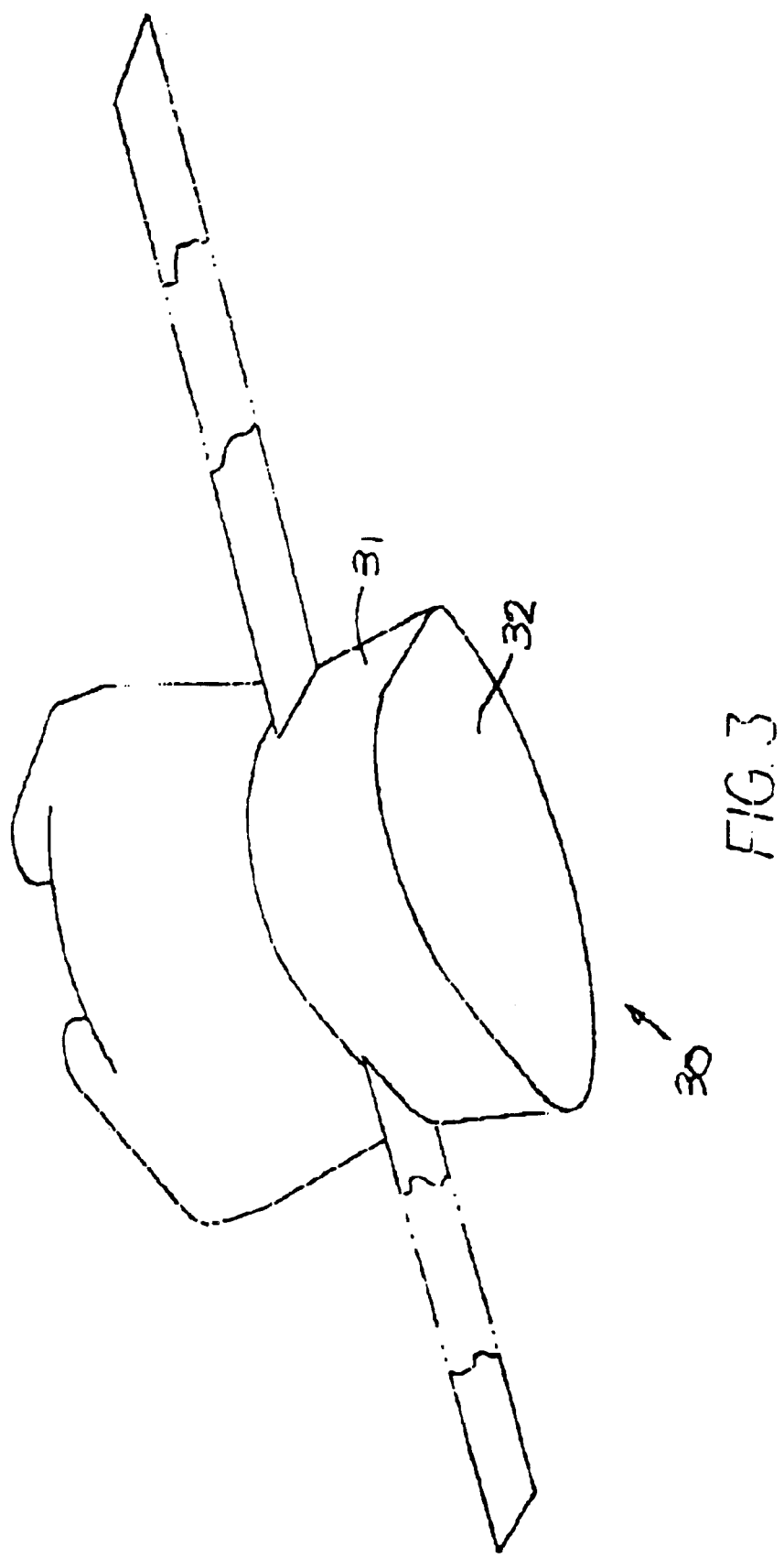
FIG. 3 is a bottom perspective view of the pad of FIG. 1.
Figure 4:
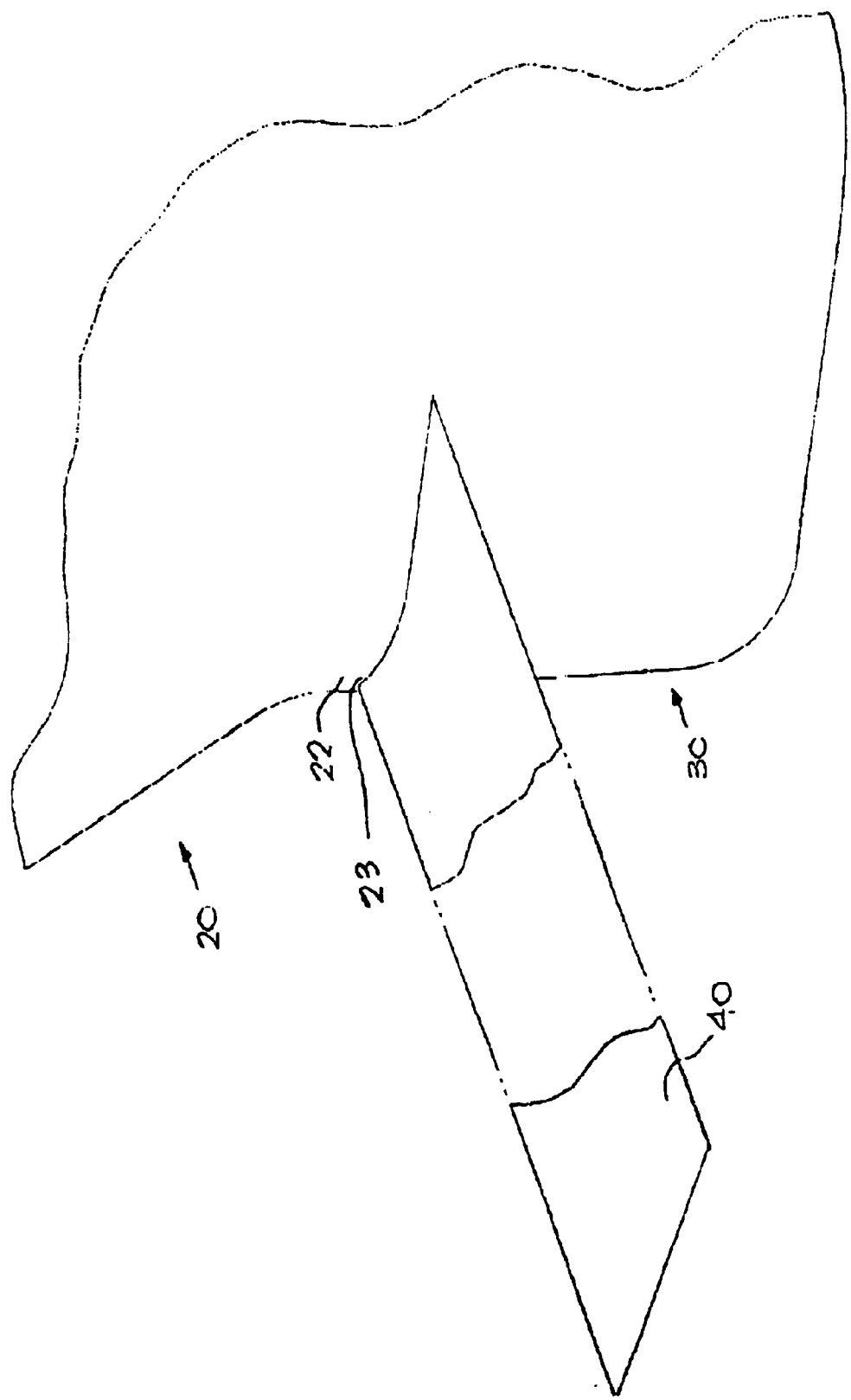
FIG. 4 shows the strap protruding through the layers of the pad of FIG. 1.

As shown in FIG. 3, the resting platform 30 of the wound covering pressure relief pad 10 has an exterior shape 31 similar to the contoured shell 20, although other shapes may be used. The primary purpose of the resting platform 30 is to provide a means for dispersing the pressure created against the patient's skin or wound when the patient exerts a downward pressure on a particular portion of the body. In the embodiment shown, the resting platform 30 has an essentially flat bottom 32 and is solid throughout the platform 30. However, depending on the materials selected for the platform 30, the platform 30 may have an essentially flat bottom 32 and be essentially hollow inside, or it 30 may have a cavity similar to the contoured shell 20, or it 30 may have plugs of material removed from predetermined positions. The specific design of the platform 30 can be modified by the user based on how the material dissipates pressure away from the contoured shell 20 and the expected orientation of the patient when the pad 10 is being used.

The shell 20 and the platform 30 are each preferably made of a resilient material capable of yielding to pressure but quickly recovering or returning to the original state, when the pressure source is removed. One example of a resilient material which has these characteristics is viscoelastic foam. Viscoelastic foams are available through several sources, such as Dynamic Systems, Inc., 235 Sunlight Drive, Leicester, N.C. 28748, which sells viscoelastic foams under the tradenames SunMate and Pudgee, and which also sells laminar cushions comprising SunMate and Pudgee foams, and through Lendell Manufacturing Inc., 5301 S. Graham Rd., St. Charles, Mich. 48655, which sells viscoelastic foam under the product labels SRF EP-3, SRF PHS-10, SRF PHS-14 and SRF CB-11. Other foams with similar characteristics may also be used.

The wound covering pad 10 also optionally includes a means to secure the shell to the heel. For example, the pad may include at least one strap 40 to hold the pad 10 to the patient's body. As shown in FIGS. 1–4, the strap 40 extends beyond the periphery 23 of the contoured shell base 22, and is preferably positioned between the contoured shell 20 and the resting platform 30, such that the strap 40 is not visible within the cavity 26. In the embodiment shown, the strap 40 is a single strip which runs continuously between the shell 20 and the platform 30. Alternatively, the strap 40 may be two separate pieces with a first piece extending from one side of the shell base and a second piece extending from the opposite side of the shell base, or the strap may be of any form that can hold the wound covering pad 10 to the target area. Because the patient is likely to have limited mobility, the strap 40 can be made of gauze, linen or other soft fabric strips, such as a low-denier cotton, polyester or polyester/ cotton blend. However, the strap 40 may be made of a more durable material or heavier weight material, including elastic materials, if so desired by the user.

As shown in FIG. 2, the wound covering pressure relief pad 10 is positioned on a patient's foot such that the patient's heel 12 lies within the cup 26, the femur 14 rests within the recession 28, and the strap 40 can wrap around the ankle 16. When positioned on the patient, the strap 40 holds the pad 10 in position, and the viscoelastic foam shell 20 and platform 30 provide cushioning for the wound or high pressure point area. If the patient is immobile, the strap 40 may be eliminated from the pad 10. Similarly, if the pad 10 is contoured to fit over or against another body region, and the patient is not expected to move, the strap 40 may be eliminated.

Figure 5:
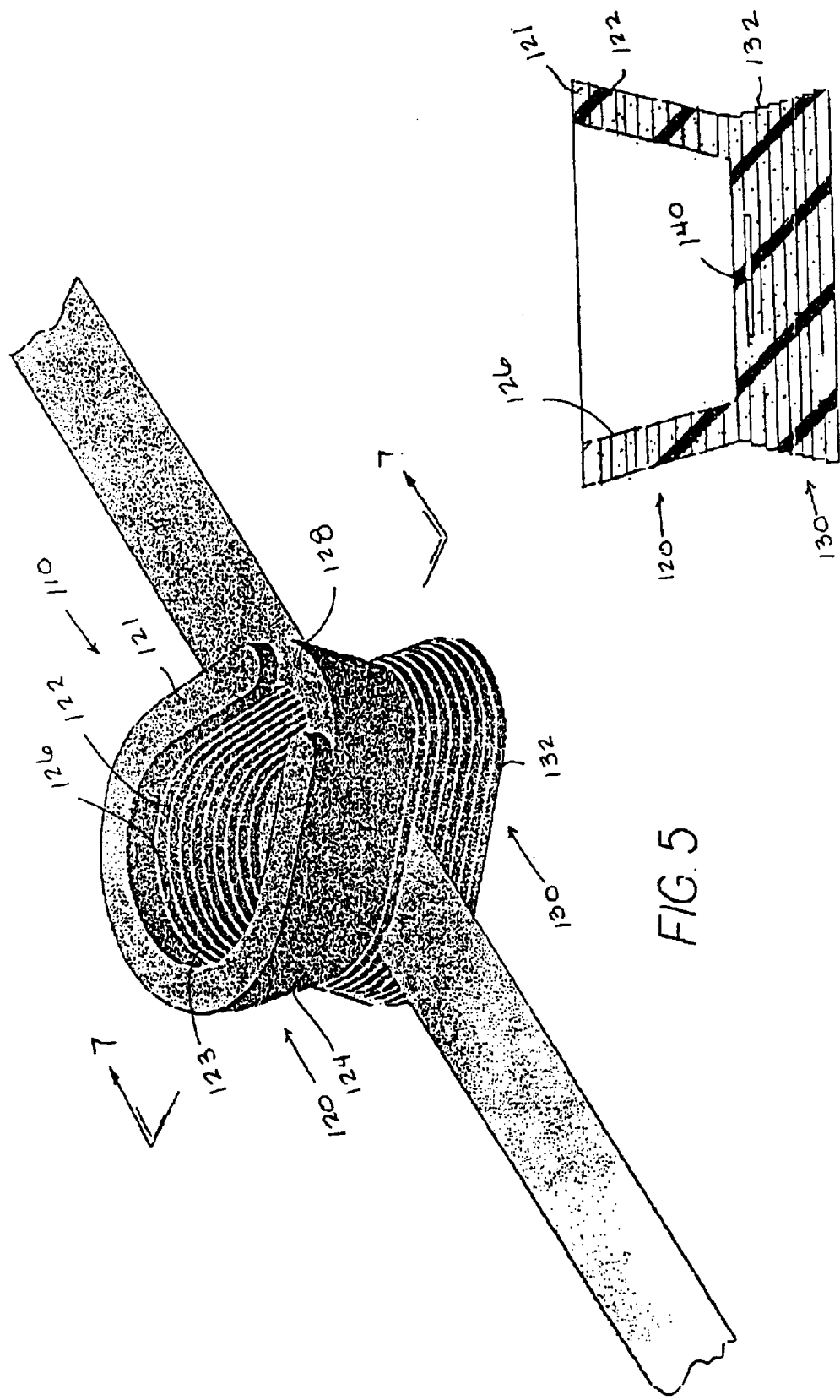
FIG. 5 is a perspective view of a first alternative embodiment of a pressure relief pad to fit over the heel made in accordance with the present invention.
Figure 6:
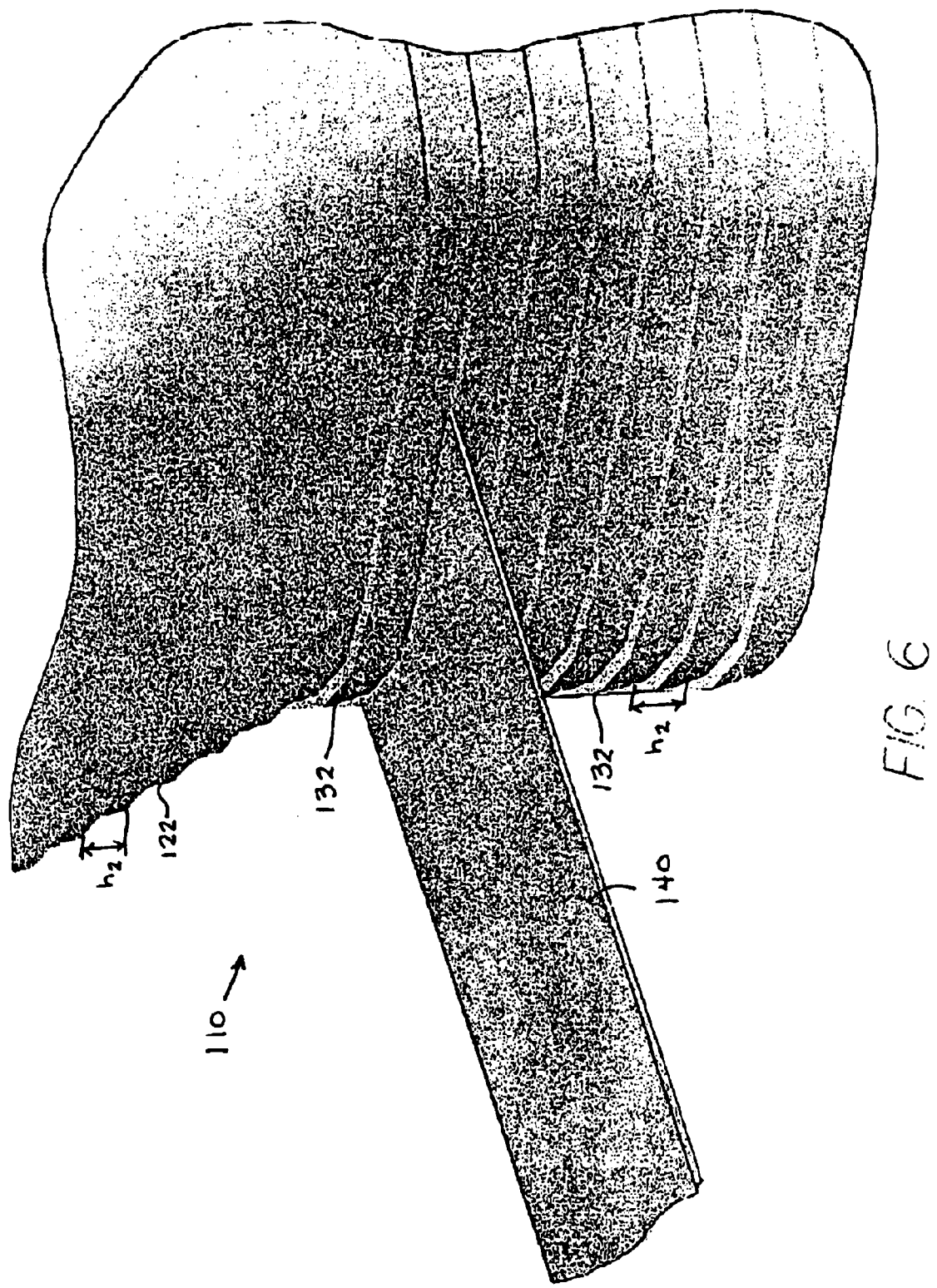
FIG. 6 shows the strap protruding through the shell layers and platform layers of the pad of FIG. 5.

An alternative embodiment 110 of a wound covering pressure relieving pad made in accordance with the present invention is shown in FIGS. 5–7. The wound covering pad 110 is essentially identical to the pad 10 of FIGS. 1–4 except that the shell 120 and the platform 130 are each made of a plurality of layers 122, 132 of cushioning foam secured together by adhesive. Each shell or cavity-side layer 122 includes an aperture 123. Further, each shell layer 122 is essentially identical except that each layer 122 is sized such that the layers 122 can be stacked to form an outwardly angled shell side 124 with a cup 126 in the center. The shell 120 has at least one top layer 121 that is not continuous, but rather is "U"-shaped. When positioned on top of the other layers 122, the top layer 121 leaves a recess 128 for accommodating a patient's leg. Each platform or base layer 132 is essentially identical except that each base layer 132 is sized such that the layers 132 can be stacked to form an angled platform 130. In the embodiment shown, the platform layers 132 are solid sheets, however, the layers 132 may include apertures if so desired by the user. Optionally, the layers of the shell 122 and of the platform 132 may be sized such that the sides of the shell 120 and/or the platform 132 are essentially straight when the layers are joined together.

The shell layers 122 and the platform layers 132 are each preferably made of a resilient material, such as the viscoelastic foams SunMate, Pudgee, or SunMate/Pudgee laminar cushions manufactured by Dynamic Systems, Inc. In a preferred embodiment, each layer 122, 132 has a height $h_2$ of about ½", although the heights $h_2$ may vary significantly as desired by the user. Further, a layered shell 120 can be paired with a one-piece platform 30, or a one-piece shell 20 can be paired with a layered platform 130. A pressure sensitive glue, hot-melt adhesive, pressure sensitive polymer, thermoplastic film, or any other adhesive known in the art which will bind the individual layers 122, 132 together can be used to secure the shell layers 122 to each other, and to secure the platform layers 132 to each other, and to secure the shell layers 122 to the platform layers 132. Different adhesives may be used between each combination of layers, if so desired.

Similar to the pad 10, the layered pad 110 may include a strap 140 for holding the pad 110 to the patient's foot. The strap 140 may be made of gauze, linen or other soft fabric strips, but may be made of a more durable material, if desired by the user. The strap 140 may also be a single strip or composed of two or more segments, as required. In the embodiment shown, the strap 140 is a single strip of gauze positioned between two layers of the platform 132 so that the strap 140 is not visible in the shell cup 126.

Figure 8:
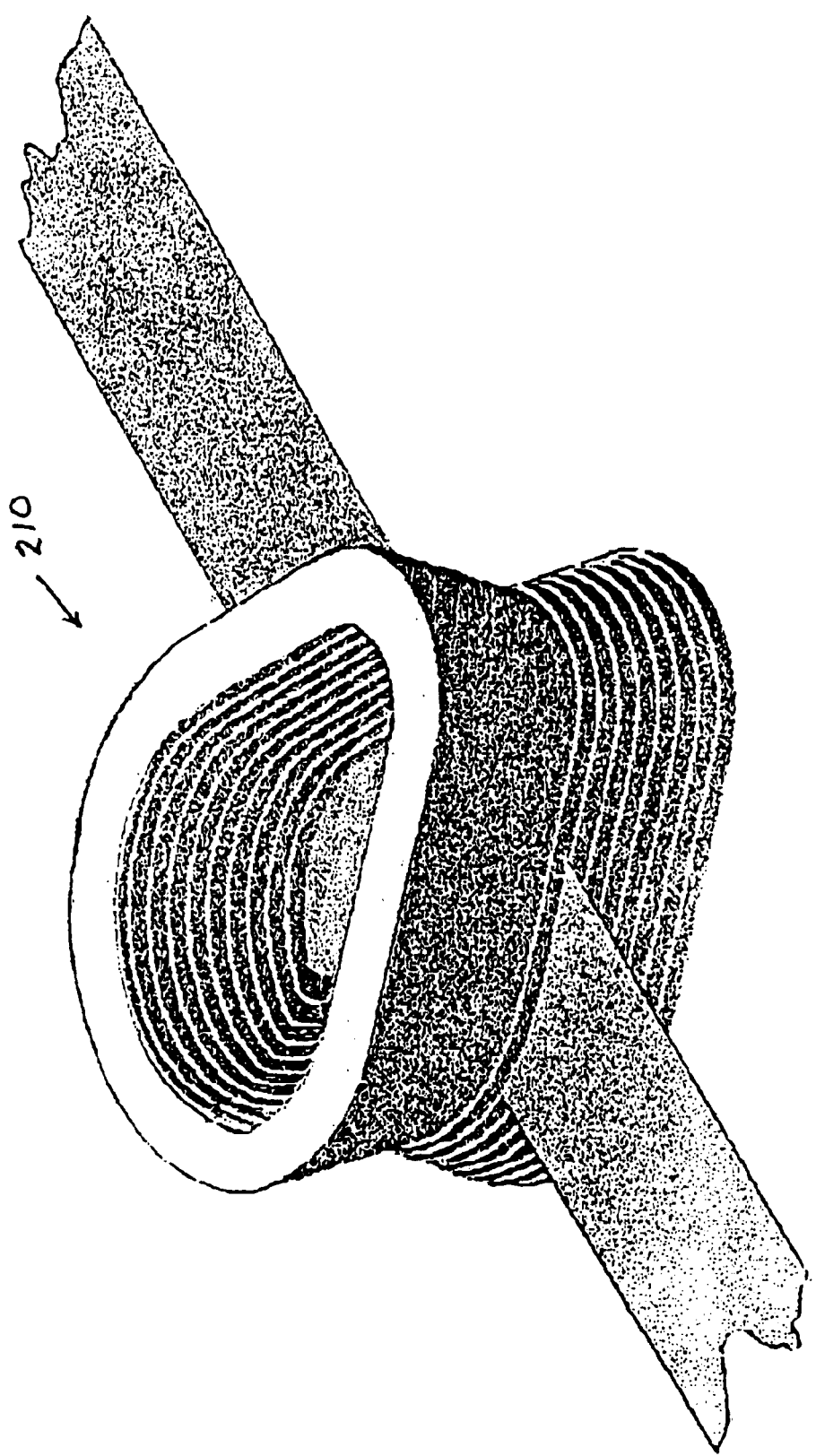
FIG. 8 is a top perspective view of a pressure relief pad similar to the pad of FIG. 5 but designed to fit over the elbow.
Figure 9:
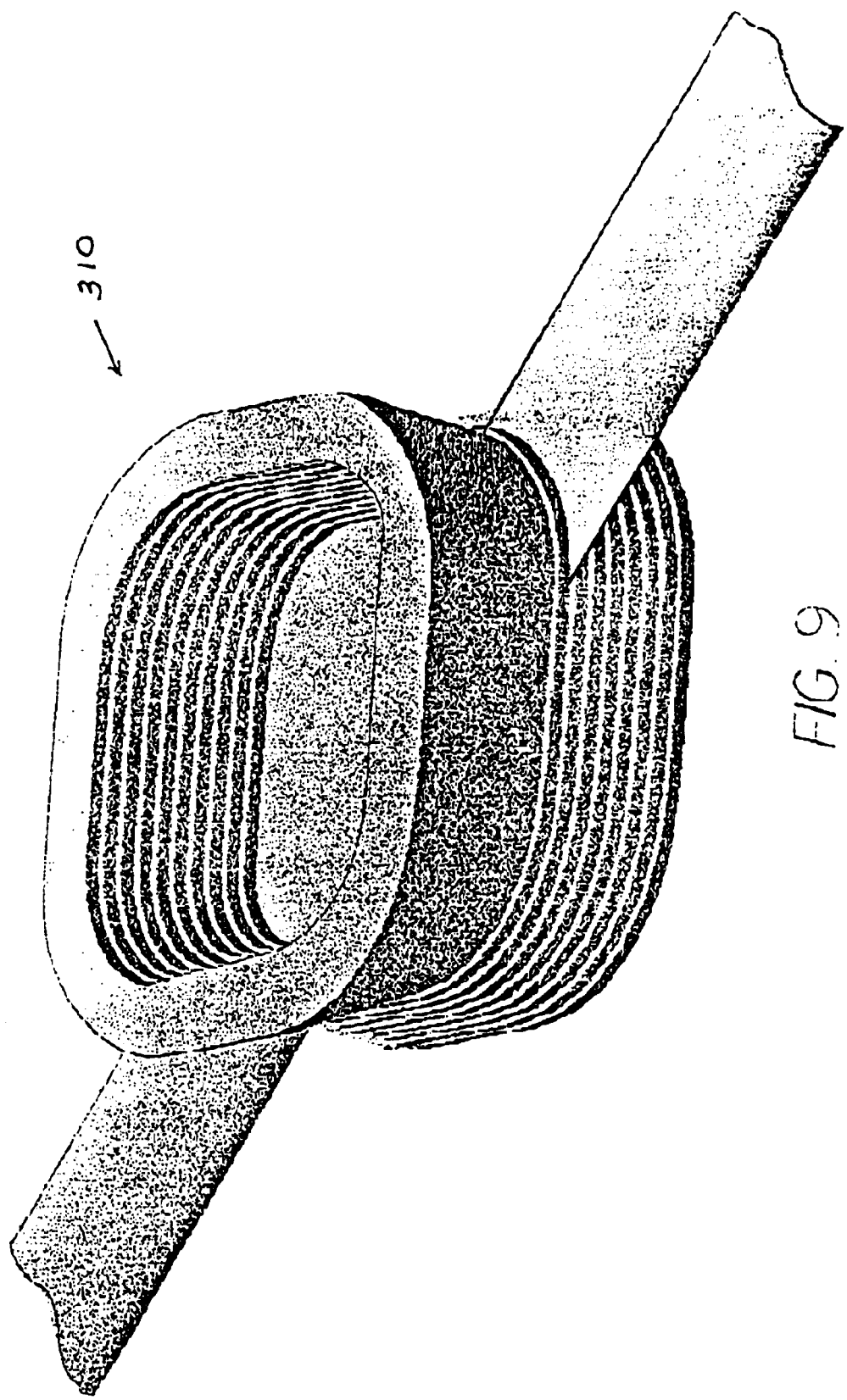
FIG. 9 is a top perspective view of a pressure relief pad similar to the pad of FIG. 5 but designed to fit against the head.
Figure 10:
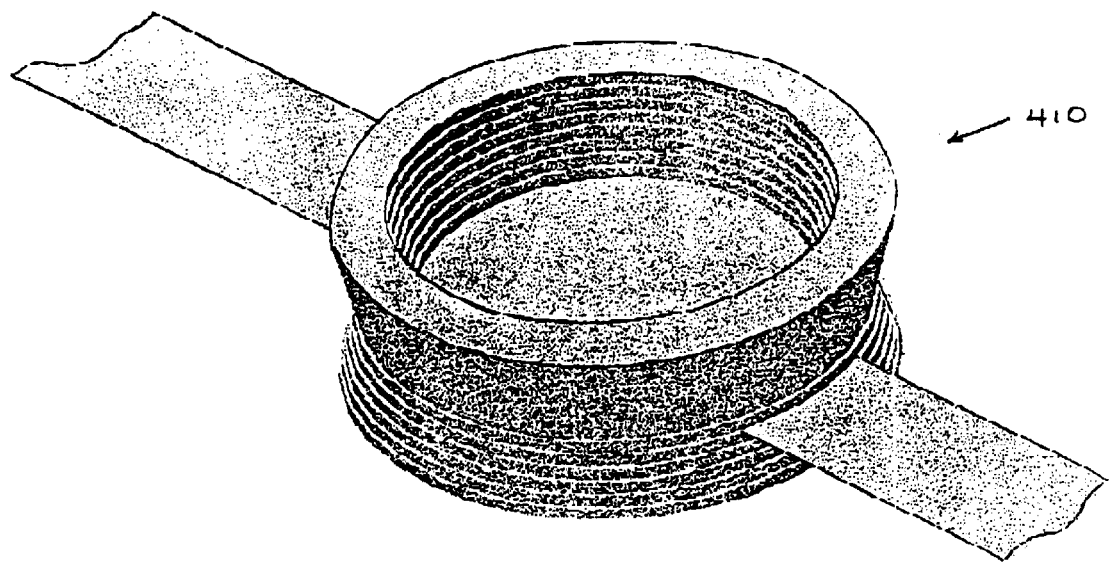
FIG. 10 is a top perspective view of a pressure relief pad similar to the pad of FIG. 5 but designed to fit against the back or hip.
Figure 11B:
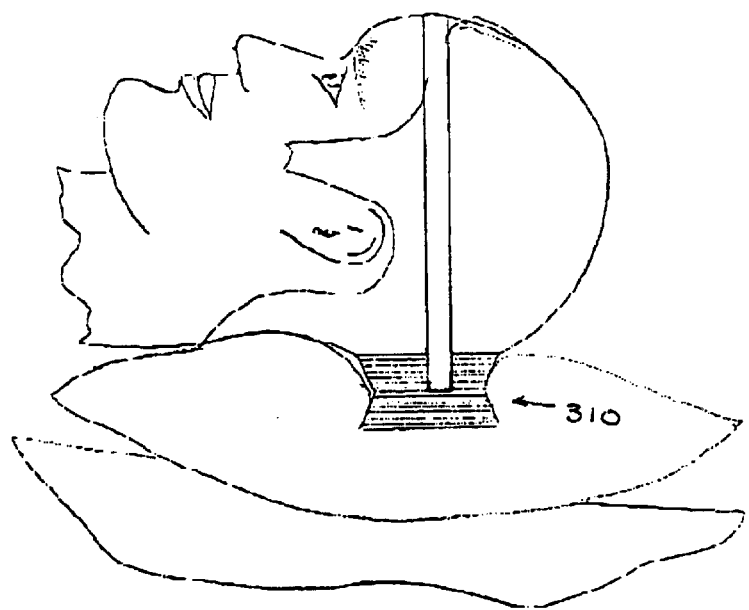
FIG. 11 A–D are side perspective views of the pads of FIG. 8–10 positioned against a patient's elbow, head, back and hip, respectively.
Figure 11C:
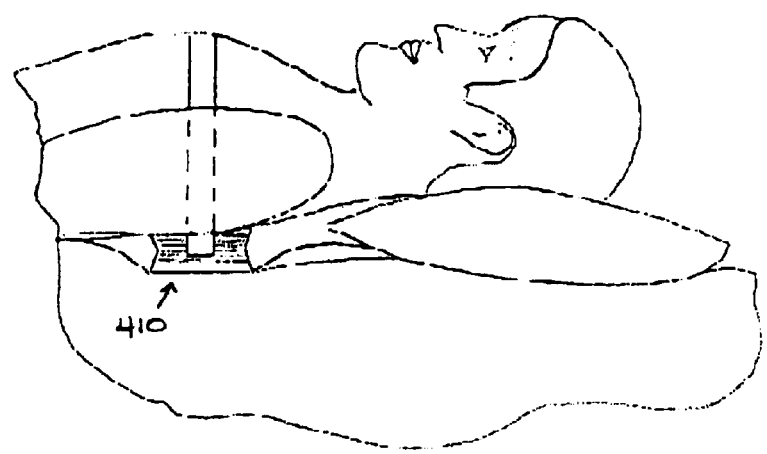
Figure 11D:
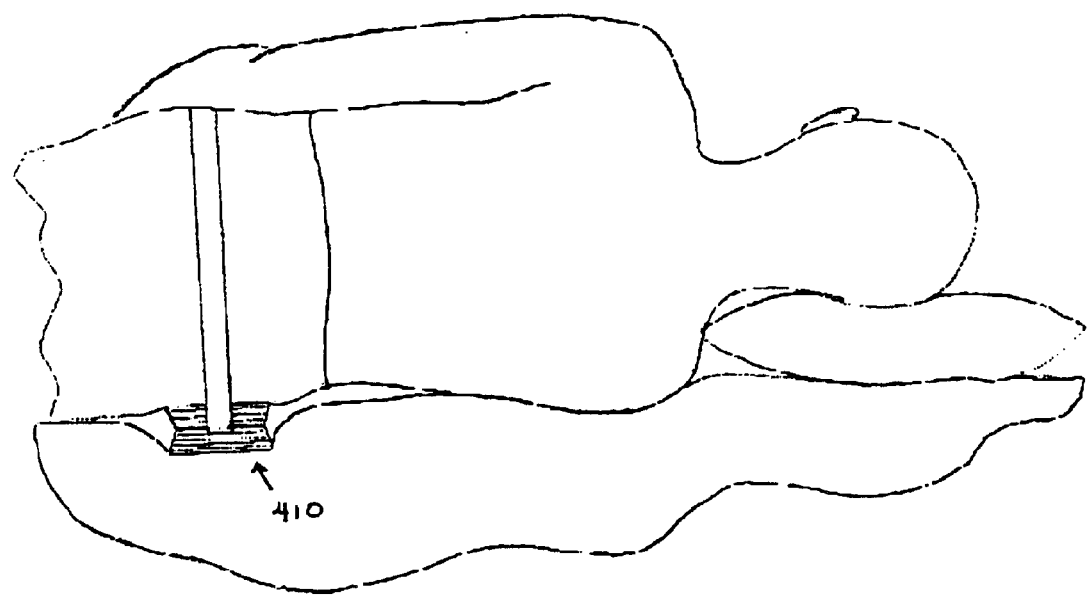

As shown in FIGS. 8–11D, the pads 10, 110 may be contoured to fit over or against other body regions. For example, an elbow pad 210 is shown in FIGS. 8 and 11A, a head pad 310 is shown in FIGS. 9 and 11B, and a back and hip pad 410 is shown in FIGS. 10, 11C and 11D. The sizes and shapes depicted are representative of types of pads which can be made utilizing the inventive features herein. Other sizes and shapes may be made as desired by the user.

Figure 12:
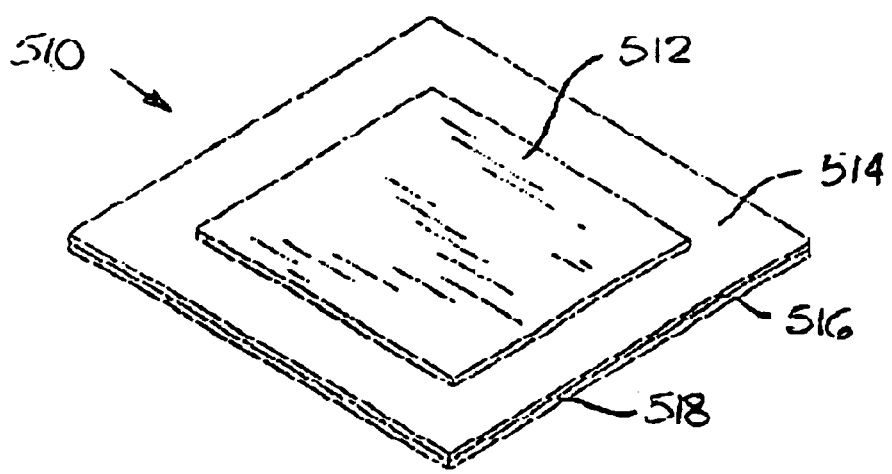
FIG. 12 is a perspective view of a second alternative embodiment of a pressure relief pad made in accordance with the present invention having an exudate absorbing material layer.
Figure 13:
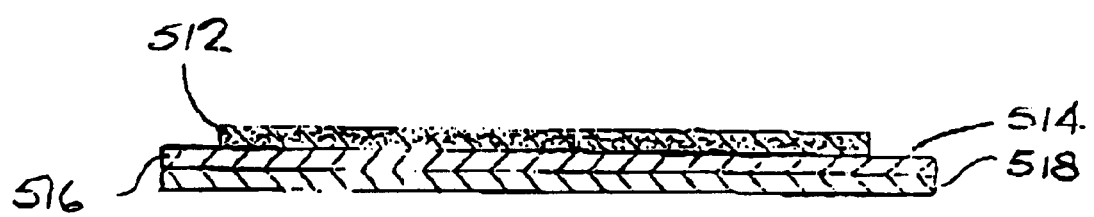
FIG. 13 is a side view of the pad of FIG. 12.

An embodiment 510 of the pressure relief pad constructed in accordance with the present invention may be used by persons suffering from decubitus ulcers or similar wounds which generate exudates. As shown in FIGS. 12 and 13, the pressure relief pad 510 includes an exudate absorbing material 512, such as a hydrophilic polyether polyurethane foam layer or similar absorbent material. The hydrophilic foam layer 512 is secured to a first layer of viscoelastic foam 516 by a thin layer of adhesive 514. In a preferred embodiment, the hydrophilic foam layer 512 is slightly smaller than the first foam layer 516, so that a ring of adhesive 514 remains exposed, and the adhesive 514 is an FDA-approved adhesive that can be placed in direct contact with the patient's skin and that will maintain reasonable adherence to the skin even when wet, such as any of a variety of FDA-approved silicone adhesives known in the art and used on colostomy pouches.

One or more additional viscoelastic foam layers 518 can be secured to the first layer 516 by any known method, such as by using adhesives or hot-melt glues. Although not required for the pad 510 to function as intended, in the embodiment shown, all the layers 516, 518 of viscoelastic foam have approximately similar lengths $L_5$ and widths $W_5$, although the thicknesses $T_5$ may vary.

In one embodiment, the hydrophilic polyether polyurethane foam layer 512 is a ¼" thick foam produced by Lendell Manufacturing Inc., St. Charles, Mich., and sold under the product label Medisponge. This foam is designed to absorb wound exudates, inhibit protein binding, and facilitate wound healing. A thin layer of silicone adhesive 514 is used to secure the absorbent foam 512 to a ½" thick pad of SRF EP-3 viscoelastic foam 516 produced by Lendell Manufacturing Inc. A second layer of viscoelastic foam 518—½" thick layer of SRF CB-11 foam produced by Lendell Manufacturing Inc.—is secured to the first foam layer 516 with a hot-melt adhesive.

The pressure relief pad 510 is designed to be positioned on a patient directly over an open wound, or over an area that has a high probability of forming an open wound, with the hydrophilic polyether polyurethane foam layer 512 being placed in direct contact with the skin and wound, the exposed section of adhesive 514 being in direct contact with the skin, and the viscoelastic layers 516, 518 facing away from the patient. When positioned on the patient, the hydrophilic foam layer 512 absorbs any exudates from the wound, the adhesive 514 holds the pad 510 in position, and the viscoelastic layers 516, 518 provide cushioning for the wound and high pressure area. Further, the viscoelastic layers 516, 518 and any air which may be trapped between the layers 516, 518 can help the rate of recovery for the wound area and can minimize the probability of reoccurrence of a similar wound by causing the pressure to be redistributed over a larger region as the viscoelastic layers 516, 518 compact and recover under pressure from the patient. Thus, by using a variety of combinations of viscoelastic foams, pressure relief pads can be produced that respond to a wide range of applied pressures.

Figures 14, 15:
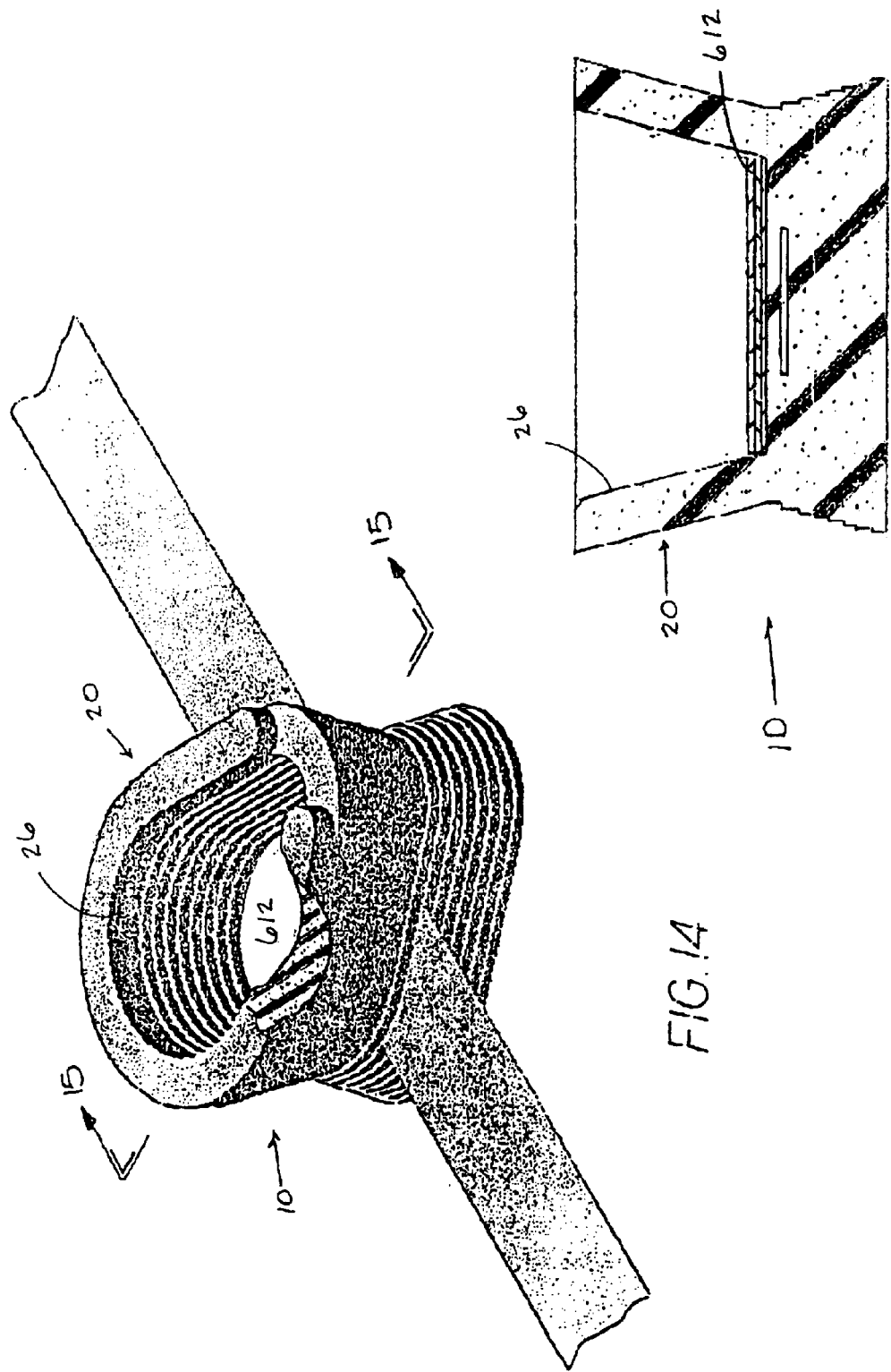
FIG. 14 is perspective view of a pressure relief pad to fit over the heel made in accordance with the present invention having an exudate absorbing material layer.
FIG. 15 is a cross-sectional view of the pad of FIG. 14 taken along line 15—15.

As shown in FIGS. 14 and 15, a hydrophilic polyether polyurethane foam layer 612 may be included in the contoured pad 10, or in any of the other contoured pads 110, 210, 310, 410. The hydrophilic foam layer 612 can be fitted into the cup 26 of the wound covering pad shell 20 to absorb any exudate from the patient's wound. Alternative, the cup 26 may be filled with a hydrophilic gel which can further relieve pressure on the wound area.

From a reading of the above, one with ordinary skill in the art should be able to devise variations to the inventive features. For example, the ribs may have different shapes or configurations, and the closure detail, such as the finger grips on the outer shell, may vary in design. These and other variations are believed to fall within the spirit and scope of the attached claims.

What is claimed:

1. A wound covering pressure relieving pad comprising:
   a. a shell, having a base with a periphery and a side projecting upwardly from said base adjacent to said periphery, wherein said base and said side form a cup contoured to accommodate a specified body part, and wherein said shell is composed of a plurality of layers of a resilient material, said layers being fixedly attached one to another, and each layer including an aperture sized and positioned to form the cup;
   b. a platform, fixedly attached to said shell base such that said platform opposes said shell, said platform being composed of a resilient foam material; and
   c. a means for reversibly securing said shell to said body part.

2. The pad of claim 1 wherein said shell layers are composed of a viscoelastic foam material.

3. The pad of claim 1 further including at least one non-continuous layer secured to said shell layers so as to form a rim on said cup, wherein said rim includes a recessed area.

4. The pad of claim 1 wherein said platform is composed of a viscoelastic foam material.

5. A wound covering pressure relieving pad comprising:
   a. a shell, having a base with a periphery and a side projecting upwardly from said base adjacent to said periphery, wherein said base and said side form a cup contoured to accommodate a specified body part;
   b. a platform, fixedly attached to said shell base such that said platform opposes said shell, said platform being composed of a resilient foam material, and wherein said platform is composed of a plurality of layer of resilient material; and
   c. a means for reversibly securing said shell to said body part.

6. The pad of claim 5 further including an exudate-absorbing material fixedly secured within said cup.

7. The pad of claim 6 wherein said exudate absorbing material is a hydrophilic polyether polyurethane foam.

8. The pad of claim 5 wherein said securing means is at least one strap, positioned between said shell and said platform.

9. The pad of claim 5 wherein said platform layers are composed of a viscoelastic material.

10. The pad of claim 8 wherein said strap is made of gauze, linen, low-denier cotton, low-denier polyester, or a combination thereof.

* * * * *